United States Patent

Brown et al.

Patent Number: 5,575,292
Date of Patent: Nov. 19, 1996

[54] APPLIED POTENTIAL TOMOGRAPHY

[75] Inventors: Brian H. Brown; David C. Barber; Francis J. McArdle, all of Sheffield, England

[73] Assignee: British Technology Group Limited, London, England

[21] Appl. No.: 170,325

[22] PCT Filed: Jun. 26, 1992

[86] PCT No.: PCT/GB92/01156

§ 371 Date: Dec. 23, 1993

§ 102(e) Date: Dec. 23, 1993

[87] PCT Pub. No.: WO93/00038

PCT Pub. Date: Jan. 7, 1993

[30] Foreign Application Priority Data

Jun. 27, 1991 [GB] United Kingdom .................... 9113830

[51] Int. Cl.$^6$ ........................................... A61B 5/05
[52] U.S. Cl. ........................................... 128/733; 128/734
[58] Field of Search ........................... 128/710, 733, 128/734; 73/632, 639, 641

[56] References Cited

U.S. PATENT DOCUMENTS

| | | | |
|---|---|---|---|
| 3,052,232 | 9/1962 | Zworkin et al. ............... | 128/733 X |
| 4,359,724 | 11/1982 | Zimmerman et al. .............. | 128/733 X |
| 4,539,640 | 9/1985 | Fry et al. . | |
| 4,572,197 | 2/1986 | Moore et al. .................. | 128/733 X |
| 4,617,939 | 10/1986 | Brown et al. . | |
| 4,660,562 | 4/1987 | House, Sr. ..................... | 128/734 X |
| 5,146,926 | 9/1992 | Cohen .............................. | 128/710 |

FOREIGN PATENT DOCUMENTS

| | | | |
|---|---|---|---|
| 0085490 | 8/1983 | European Pat. Off. . | |
| 0343928 | 11/1989 | European Pat. Off. ............. | 128/734 |
| 2354079 | 1/1978 | France . | |
| 1512564 | 10/1989 | U.S.S.R. ......................... | 128/734 |
| 2119520 | 11/1983 | United Kingdom . | |
| 2160323 | 12/1987 | United Kingdom . | |
| 2246634 | 12/1993 | United Kingdom . | |
| WO8909564 | 10/1989 | WIPO . | |

*Primary Examiner*—Sam Rimell
*Attorney, Agent, or Firm*—Cushman, Darby & Cushman

[57] ABSTRACT

In an APT method, the surface-contact electrodes are located in a closed loop or rosette array on one planar, or nominally planar, skin surface of a body to be investigated, and electrically connected to data acquisition and processing equipment. The invention also includes apparatus for carrying out this method, comprising an array of surface-contact electrodes (8), adapted to be applied to the skin of a body to be investigated, the electrodes (8) being arranged on a flexible carrier (10) in a closed loop, or rosette formation on one common plane, or nominal plane.

11 Claims, 4 Drawing Sheets

APPLIED POTENTIAL TOMOGRAPHY

FIELD OF THE INVENTION

This invention relates to applied potential tomography (APT) to achieve electrical impedance imaging.

APT techniques have been described in GB 2119520, GB 2160323, WO 89/09564, or GB 9013177.2 which permit the electrical impedance changes which occur within a conducting body to be imaged. The electrical impedance changes are measured by applying electrical currents to, and measuring the differences of electrical potential between, a number of electrodes placed around the boundary of a plane through the conducting body, e.g. the thorax, which is circumscribed by a plurality of spaced apart electrodes. An algorithm has been described which permits the measurements thus obtained to be converted into an image of the electrical impedance changes which have occurred since some reference time. The impedance changes represented in these images may have occurred at any point in the conducting body. The image value depends upon the products of the true size of the impedance change and a sensitivity factor which may vary with position inside the body. This sensitivity factor has maximum value in the plane of the electrodes and diminishes with increasing distance from that plane. It is clear that if no significant impedance changes occur in the plane of the electrodes, then the technique can be used to image impedance changes which occur off-plane at other locations in the body.

In some circumstances however, it is difficult or undesirable to place the electrodes around a plane that will pass through the origin of the impedance change.

In situations where all impedance changes occur deep within the conducting body, and no significant changes occur at or near the surface, the electrode plane can be placed on the surface of the body and used to image the impedance changes beneath the electrode plane. In the human body, for example, large impedance changes occur in the heart during the cardiac cycle but comparatively little impedance change occurs in the skin over the same time period.

SUMMARY OF THE INVENTION

According to a first aspect of the present invention, there is provided an APT method for investigating a region within a body in which a plurality of surface-contact electrodes are located in a closed loop or rosette array on one planar, or nominally planar, skin surface of the body distant from the region under investigation, the electrodes being electrically connected to data acquisition and processing equipment.

According to a second aspect of the present invention, there is provided apparatus for use in carrying out the above defined method, comprising a plurality of surface-contact electrodes arranged on a common flexible carrier applicable to a planar or nominally planar skin area of a body to be investigated, to locate said electrodes in a closed loop, or rosette array on said area.

Thus, with the method and apparatus of the invention, if for instance the planar, or nominally planar surface is the anterior surface of the human chest, in the vicinity of the heart, images can be produced of the impedance changes within the heart using an overlying surface electrode plane, for by confining all measurement electrodes to one surface of the conducting body, the impedance imaging technique may be used where it is difficult or undesirable to place the electrodes around a plane that will pass through the origin of the impedance change. However, this electrode arrangement will usually be limited to those situations e.g. heart investigations, where the impedance changes in the surface electrode plane are not significant.

In one embodiment, the electrodes may be attached around the perimeter of a preferably circular, and preferably transparent carrier—a synthetic plastics material being particularly suitable. A thin, flexible sheet of synthetic plastics material is particularly suitable, which sheet may be of circular or annular form. For a rosette array of 16 electrodes, a circular carrier may be marked-out with radii at 22.5° on each of which an electrode is approximately located, while location may be by adhesive between the carrier and an attachment tongue of an electrode mounting strip.

DETAILED DESCRIPTION OF PREFERRED EMBODIMENT

Figure 1:
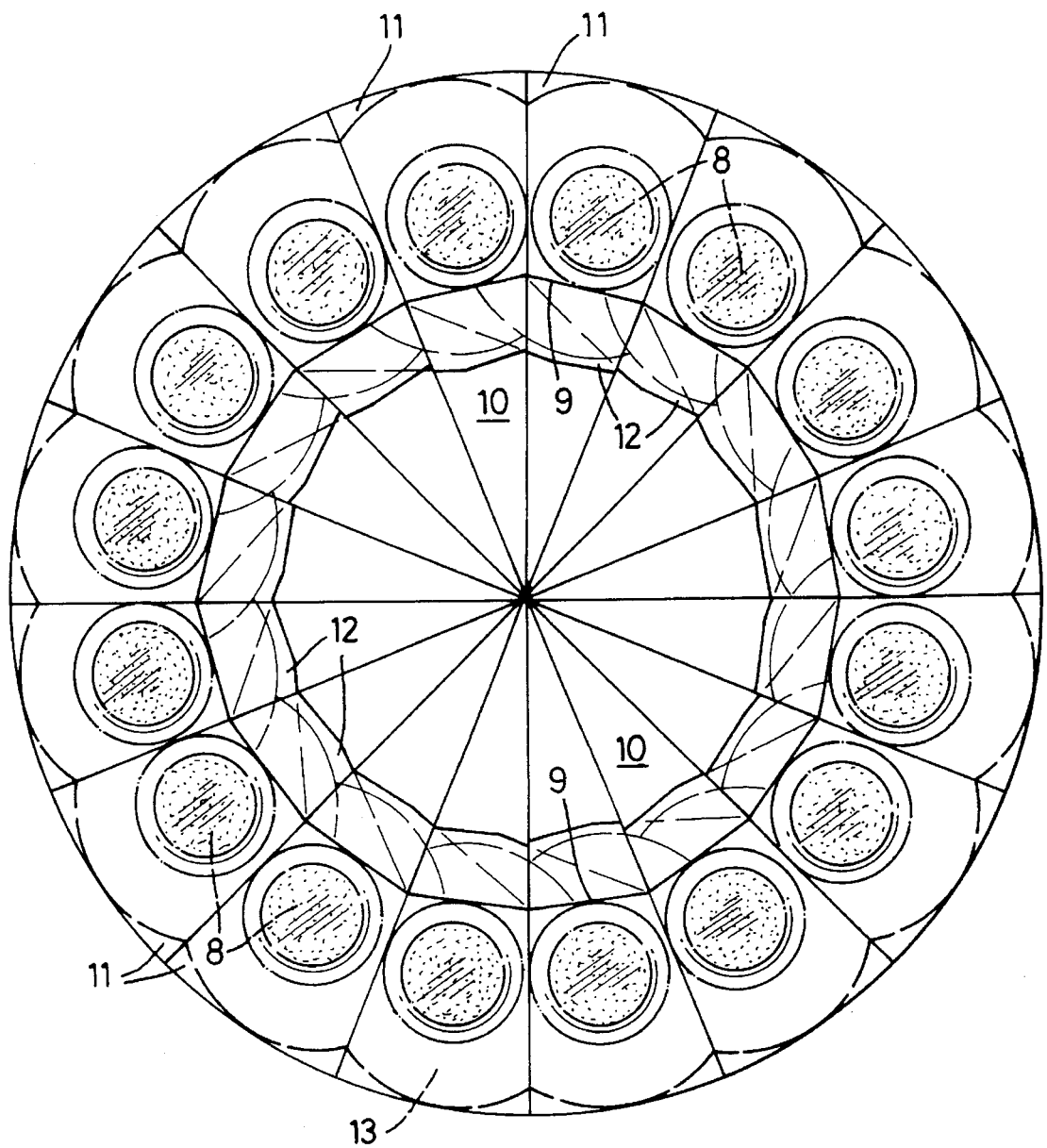
FIGS. 1 and 2 show respectively front and rear views of apparatus in the form of a circular, rosette array of sixteen electrodes.

The electrode array of the apparatus illustrated in FIG. 1 is adapted to be positioned on the anterior surface of the human chest, e.g. for investigations of the heart. Sixteen electrodes (8) are attached around the perimeter (9) of a flexible, circular, transparent plastic carrier (10), each electrode (8) being secured to a mounting strip (11) provided with an attachment tongue (12) by which the mounting strip (11) is secured, by adhesive, to the carrier (10). Each mounting strip (11) is also secured by adhesive to a resilient, foam like quadrant (13) of synthetic plastics material through which a contact (14) of each electrode (8) passes for connection to a suitable lead (not shown) to convey the measured electrical impedance changes to APT processing equipment.

Figure 2:
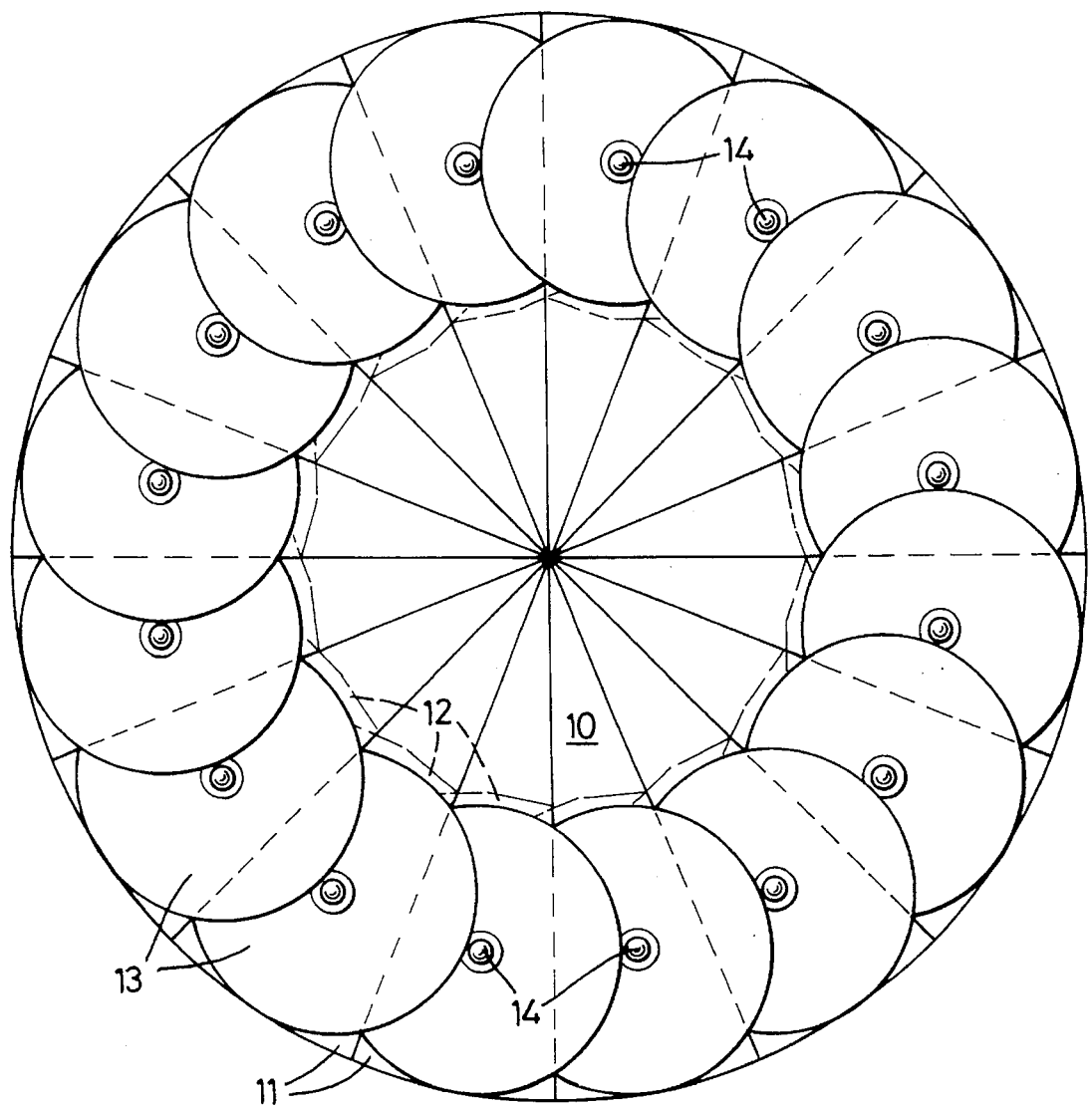
Figure 3:
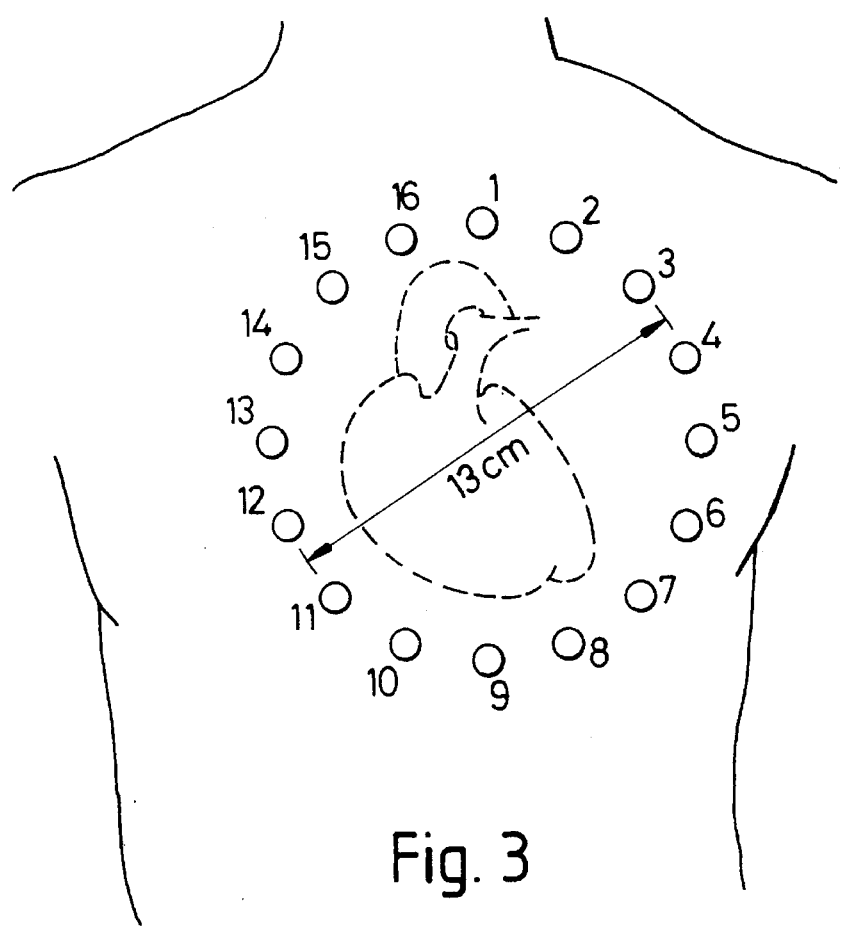
FIG. 3 shows the apparatus of FIGS. 1 and 2 applied to the anterior surface of a human chest.

As illustrated in FIG. 3, to produce images of the heart, the circular array of electrodes of FIGS. 1 and 2 is centred on the left sternal edge of the third intercostal space and have a diameter of around 13 cm.

Figure 4:
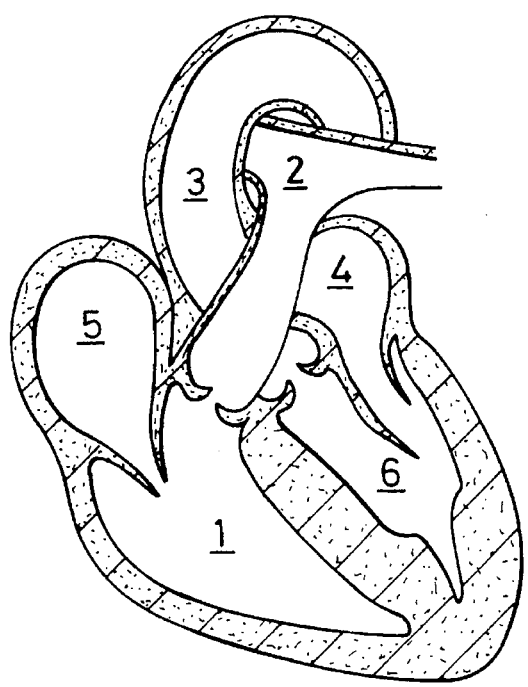
FIG. 4 shows the heart.
Figure 5:
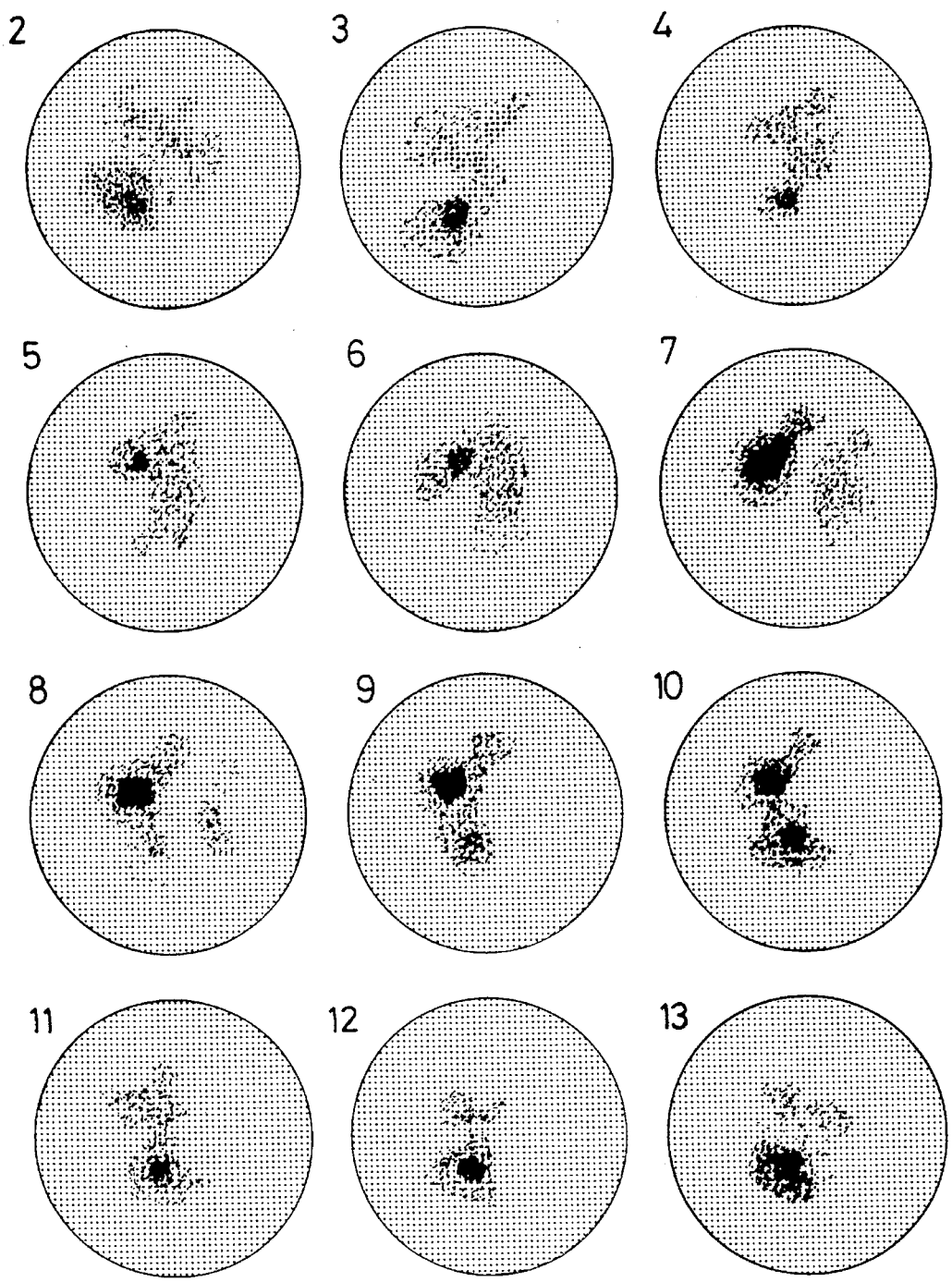
FIG. 5 shows the image sequence produced by the apparatus of FIGS. 1 and 2 using the so-called Sheffield APT system.

Considering FIGS. 4 and 5, image 2 of FIG. 5 shows increased conductivity (darker shades) in the right ventricle (1) at end-diastole. As the ventricles contract in systole, blood is pumped into the pulmonary trunk (2) and aortic arch (3) while blood returning to the heart starts to fill the left (4) and right (5) atria. The sequence of images 3 to 7 of FIG. 5 show the conductivity increases in these regions while the blood volume is increased. Finally, in diastole, blood flows from the right atrium (5) into the right ventricle (1) which is evident in images 8 to 13. At the same time blood also flows from the left atrium (4) into the left ventricle (6) but this is not evident in the APT image sequence presumably because the left ventricle is deeper than the right and thus less clearly seen.

We claim:

1. A method for investigating a region within a body by applied potential tomography, comprising:

locating a plurality of surface-contact electrodes in a closed loop array on one substantially planar skin surface of the body distant from the region under investigation, applying electrical signals to said electrodes, and measuring electrical signals responsive to said applied signals at said electrodes, the electrodes being electrically connected to data acquisition and processing equipment.

2. Apparatus for use in investigating a region within a body by applied potential tomography, comprising a plurality of surface-contact electrodes arranged on a common flexible carrier applicable to a substantially planar skin area of the body to be investigated, to locate said electrodes in a closed loop array surrounding a generally electrode-free area on the skin area.

3. Apparatus as claimed in claim 2, wherein the carrier is circular.

4. Apparatus as claimed in claim 2, wherein the carrier is annular.

5. Apparatus as claimed in claim 3 or claim 4, wherein the electrodes are attached around the perimeter of the carrier.

6. Apparatus as claimed in any one of claim 2, wherein the carrier is transparent.

7. Apparatus as claimed in any of claims 2 to 6, wherein the carrier is of synthetic plastics material.

8. Apparatus as claimed in claim 7, wherein the carrier consists of a thin, flexible sheet or annulus of synthetic plastic material.

9. Apparatus as claimed in claim 2, wherein, the plurality of electrodes comprise a 16 electrode rosette, each electrode of the plurality of electrodes being at least approximately located 22.5° apart.

10. Apparatus as claimed in claim 2, wherein each of the plurality of electrodes is provided with a mounting strip having an attachment tongue.

11. Apparatus as claimed in claim 10, wherein each of the plurality of electrodes is secured to the carrier by adhesive between the carrier and the attachment tongue.

\* \* \* \* \*